US00PP20811P3

(12) United States Plant Patent
Ruter

(10) Patent No.: US PP20,811 P3
(45) Date of Patent: Mar. 9, 2010

(54) ***HIBISCUS* PLANT NAMED 'PANAMA BRONZE'**

(50) Latin Name: ***Hibiscus acetosella*×*Hibiscus radiatus***
Varietal Denomination: Panama Bronze

(75) Inventor: John Ruter, Tifton, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 11/881,930

(22) Filed: Jul. 30, 2007

(65) Prior Publication Data

US 2009/0038041 P1 Feb. 5, 2009

(51) Int. Cl.
*A01H 5/00* (2006.01)

(52) U.S. Cl. ..... Plt./257

(58) Field of Classification Search ..... Plt./257
See application file for complete search history.

(56) References Cited

U.S. PATENT DOCUMENTS

PP11,772 P2 2/2001 Bergman
PP11,854 P2 5/2001 Fleming et al.
PP11,857 P2 5/2001 Fleming et al.
PP13,631 P2 3/2003 Fleming et al.
PP13,745 P2 4/2003 Zwetzig et al.
PP13,746 P2 4/2003 Zwetzig et al.
PP13,752 P2 4/2003 Zwetzig et al.
PP13,913 P3 6/2003 Fleming et al.
PP15,091 P2 8/2004 Whitcomb
PP16,155 P3 12/2005 Leue
PP16,286 P2 2/2006 Mostul
PP16,669 P3 6/2006 Fleming et al.

*Primary Examiner*—June Hwu
(74) *Attorney, Agent, or Firm*—Davis Wright Tremaine LLP

(57) ABSTRACT

*Hibiscus* 'Panama Bronze' is an ornamental variety, crossed and cultivated in Georgia. The plants of the new *Hibiscus* variety display new growth with an intense bronze color in high light that matures to a green color with bronze edging, deeply cut foliage, stable foliage color, very large flowers, thrives in hot an humid conditions, and flowers heavily during short days (November to April) in zone 10. 'Panama Bronze' can be grown in the garden or in a container.

4 Drawing Sheets

Latin name: *Hibiscus* 'Panama Bronze' is of the genus and species *Hibiscus acetosella*×*Hibiscus radiatus*.

Varitey denomination: The new *Hibiscus* claimed is of the variety denominated 'Panama Bronze.'

CROSS-REFERENCE TO RELATED APPLICATIONS

This patent application is related to U.S. application Ser. No. 11/881,889, invented by the same Inventor, assigned to the same Assignee, and filed simultaneously with, the present application. Cross-reference application *Hibiscus* 'Panama Red' is the material parent plant of the present *Hibiscus* 'Panama Bronze.'

BACKGROUND OF THE INVENTION

The present invention relates to a new and distinct cultivar of *Hibiscus*, botanically known as *Hibiscus acetosella*×*Hibiscus radiatus*, and herein referred to as 'Panama Bronze.'

The new *Hibiscus* is a product of a planned breeding program conducted by the Inventor in Tifton, Ga. The objective of the *Hibiscus* breeding program is to create new plant cultivars with ornamental leaf distinctions and abundant flowers.

The new *Hibiscus* originated from a cross-pollination made by the Inventor during 2005, of the Hibiscus acetosella 'Panama Red' (co-pending U.S. patent application Ser. No. 11/881,889) as the female and *Hibiscus radiatus* (not patented) as the male, or pollen parent. The cultivar 'Panama Bronze' was discovered and selected by the Inventor as a flowering plant within the progeny of the stated cross-pollination in a controlled environment in 2006.

Asexual reproduction of the new *Hibiscus* by vegetative terminal cutting in a controlled environment in Tifton, Ga. since 2006, has shown that the unique features of this new *Hibiscus* are stable and reproduced true to type in successive generations.

BRIEF SUMMARY OF THE INVENTION

The cultivar 'Panama Bronze' has not been observed under all possible environmental conditions. The phenotype may vary somewhat with variations in environment and cultural practices such as temperatures and light intensity without, however, any variance in genotype.

The following traits have been repeatedly observed and are determined to be the unique characteristics of 'Panama Bronze:'

1. Bronze color of new foliage in high light;
2. Deeply cut foliage;
3. Stable foliage color;
4. Very large flowers;
5. Flowers heavily during short days (November to April) in zone 10; and
3. Thrives in hot and humid conditions.

Plants of the new *Hibiscus* can be compared to plants of the female parent, the cultivar 'Panama Red.' Plants of the new *Hibiscus* differ from 'Panama Red' in the following characteristics:

1. Plants of the new *Hibiscus* display an intense bronze color of new foliage under full sun (high light) conditions, compared to the female parent that shows a nearly blackish-purple under full sun (high light) conditions.
2. Plants of the new *Hibiscus* have flowers that are one third larger compared to the female parent.
3. Plants of the new *Hibiscus* have more deeply cut and elongated foliage compared to the female parent.
4. Plants of the new *Hibiscus* are less dense compared to the female parent.

Plants of the new *Hibiscus* can be compared to plants of the male parent, the *Hibiscus radiatus*. Plants of the new *Hibiscus* differ from *Hibiscus radiatus* in the following characteristics:

1. Plants of the new *Hibiscus* display an intense bronze color of new foliage under full sun (high light) conditions, compared to the male parent that shows green color under full sun (high light) conditions.
2. Plants of the new *Hibiscus* display darker and larger flowers than the male parent.

DETAILED BOTANICAL DESCRIPTION

Figure 1:
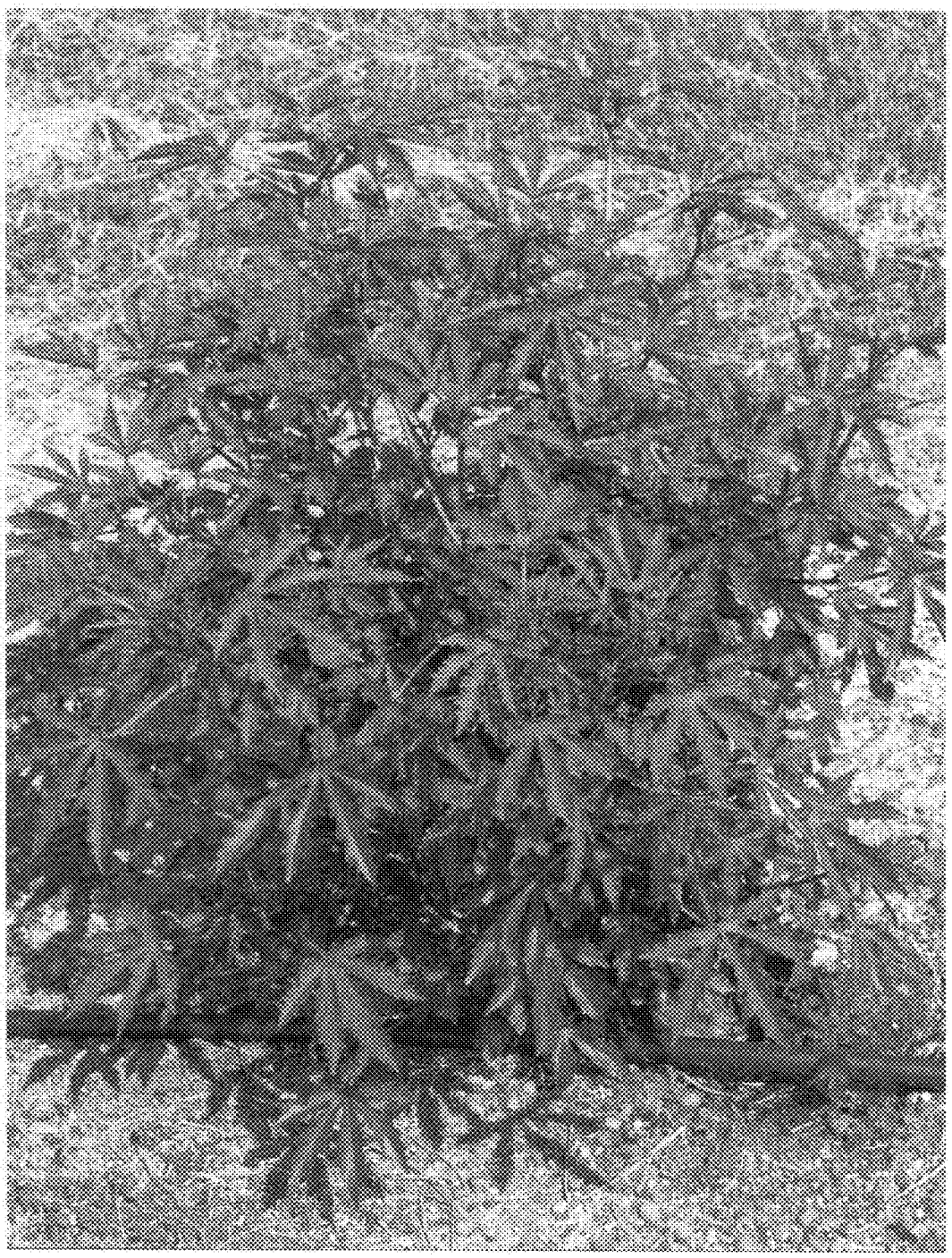
FIG. 1 is a photograph of full plant of 'Panama Bronze' in high light near full maturity.
Figure 2:
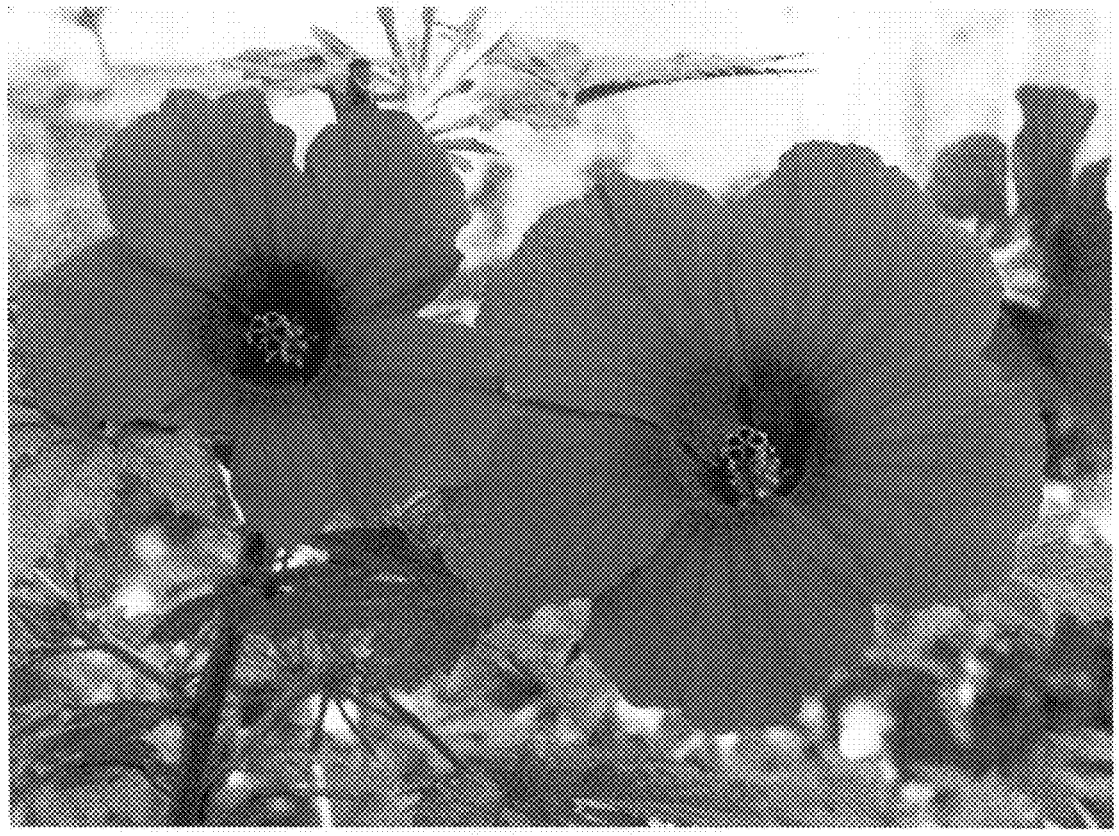
FIG. 2 is a photograph of a flower of 'Panama Bronze' showing the large, dark color of the corolla tube in the center of the flower before the petals flare out.
Figure 3:
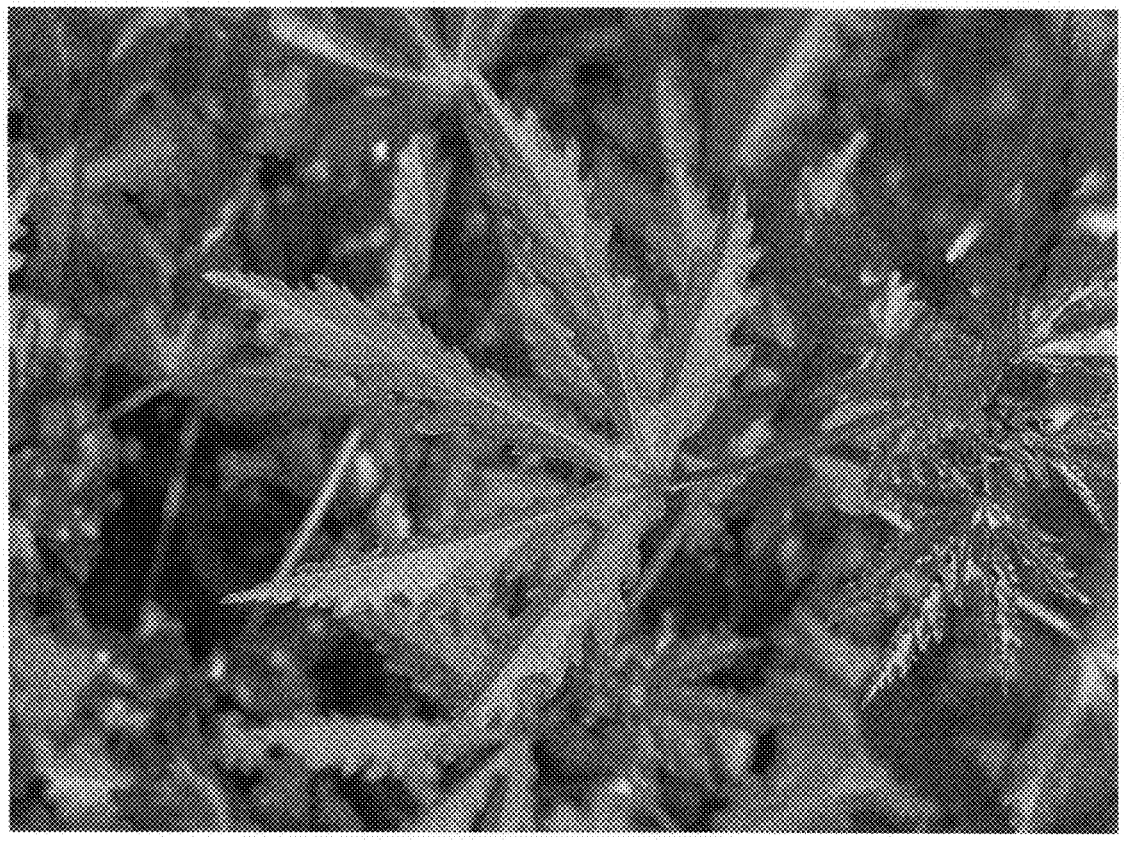
FIG. 3 is a photograph of a leaf of 'Panama Bronze' in high light showing the unique bronze edge color of the foliage near full maturity.
Figure 4:
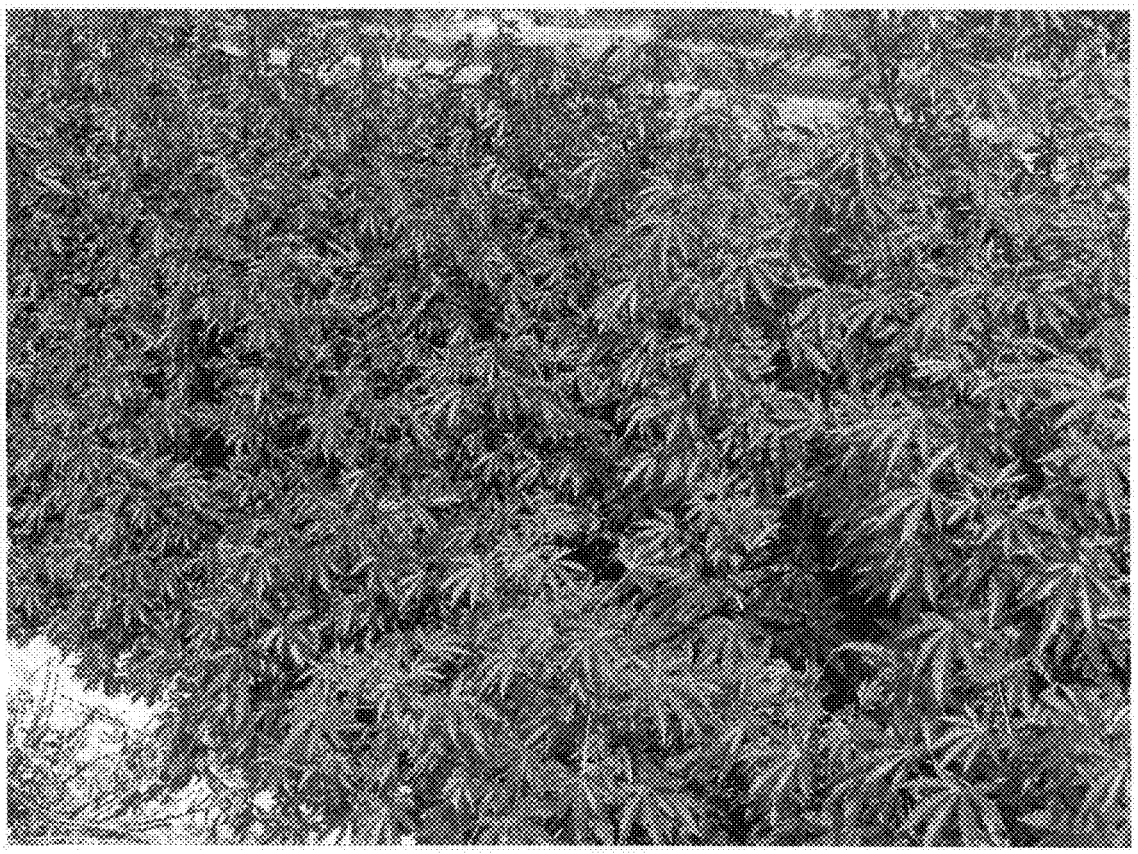
FIG. 4 is a photograph showing 'Panama Red' variety on the left and new variety 'Panama Bronze' on the right.

The following observations, measurements and values describe plants grown in Athens, Ga., by Allan Armitage and Stephanie Anderson. During the growing of the plants, day temperatures ranges from 50° F. to 100° F. and night temperatures ranges from 35° F. to 80° F. In the description, color references are made to The Royal Horticultural Society (R.H.S.) Colour Chart, 1995, Edition, except where general terms of ordinary dictionary meaning are used.

I. Habit: Round to upright.

II. Size of plant:

*A. Height.*—3–5' (0.9–1.5 m).

*B. Width.*—1–3' (0.3–0.9 m).

III. Stem:

*A. Color* (*RHS*).—187A.

*B. Length.*—2–3' (0.6–0.9 m).

*C. Diameter.*—3–5 mm.

*D. Pubescence.*—none.

*E. Shape.*—round.

*F. Odor* (*of bruised stem*).—none.

*G. Internode length.*—4–5 cm.

IV. Leaf:

*A. Color.*—(*RHS*) 1. High light: a. Upper: New growth about Orange Red RHS N34B, maturing to about Green RHS 139A with an edge color of about Orange Red RHS N34B. b. Lower: About Yellow-green RHS 148B.

*B. Mature size* (*L×W*).—8.5×8 cm.

*C. Apex.*—Acuminate.

*D. Base.*—Truncate.

*E. Margin.*—Crenate.

*F. Shape.*—Palmate.

*G. Lobes* (*present/absent*).—1. number: 3–5.

*H. Pubescence.*—None.

*I. Arrangement on stem.*—Alternate.

*J. Venation.—Pinnipalmate.*

*K. Texture.—Glabrous.*

V. Petiole:

*A. Length.*—6–7 cm.

*B. Shape.—round.*

*C. Color* (*RHS*).—139B.

*D. Pubescence.*—None.

*E. Diameter.*—0.3 cm.

VI. Flower:

*A. Inflorescence.*—None, solitary. 1. Number of individual flowers per stem:—5–10. 2. Average size of fully opened flower: 10–12 cm. 3. Lastingness of bloom: 1 day. 4. Flower season: November through April.

*B. Individual flower.*—1. Axillary, terminal: axillary. 2. Symmetry: radial. 3. Petals: 5. a. size (L×W): 5.75×4.5 cm. b. shape: spatulate. c. apex: rounded. d. base: truncate. e. margin: entire. f. color at peak of bloom: 1) apex: 187C. 2) base: 187A. 4. Pedicels: a. color (RHS): 187C. b. pubescence: none. c. length: 1–2mm. 5. Sepals: a. number: 5. b. size(L×W): 1.6 ×0.8 cm. c. shape: linear. d. pubescence: none. e. color low surface(RHS): 144B. 6. Stamens: a. number: 23–25. b. size (L×W): 0.4×0.8 cm. c. color (RHS): 163A. e. pubescence: none. 7. Pistils: a. number: 1. b. size of style (L×W): 2.5×0.3 cm. c. color of style (RHS): 185B. d. color of stigma (RHS): 187A. 8. Bracts: a. number: 9–11. b. size (L×W): 1.8×0.5 cm. c. color, lower (RHS): 126A. d. shape: spatulate.

C. Fruit: No fruit seen.

D. Seed: No seed seen.

The invention claimed is:

1. A new and distinct variety of *Hibiscus* plant named 'Panama Bronze', substantially as illustrated and described herein.

* * * * *